US011840723B2

(12) United States Patent
LaBaer et al.

(10) Patent No.: US 11,840,723 B2
(45) Date of Patent: *Dec. 12, 2023

(54) METHODS FOR DETECTION AND QUANTIFICATION OF INFECTIOUS CARBAPENEM RESISTANT ENTEROBACTERIACEAE (CRE)

(71) Applicants: Arizona Board of Regents on Behalf of Arizona State University, Scottsdale, AZ (US); Mayo Foundation for Medical Education and Research, Rochester, MN (US)

(72) Inventors: Joshua LaBaer, Chandler, AZ (US); Vel Murugan, Chandler, AZ (US); Merica Vorachitti, Phoenix, AZ (US); Rahul Pannala, Scottsdale, AZ (US); Douglas Faigel, Scottsdale, AZ (US)

(73) Assignees: Arizona Board of Regents on behalf of Arizona State University, Scottsdale, AZ (US); Mayo Foundation for Medical Education and Research, Rochester, MN (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/346,008

(22) Filed: Jun. 11, 2021

(65) Prior Publication Data
US 2021/0381028 A1   Dec. 9, 2021

Related U.S. Application Data

(63) Continuation of application No. 16/172,379, filed on Oct. 26, 2018, now Pat. No. 11,060,133.

(60) Provisional application No. 62/577,359, filed on Oct. 26, 2017.

(51) Int. Cl.
*C12Q 1/6806* (2018.01)
*C12Q 1/6851* (2018.01)
*C12Q 1/689* (2018.01)

(52) U.S. Cl.
CPC ........... *C12Q 1/6806* (2013.01); *C12Q 1/689* (2013.01); *C12Q 1/6851* (2013.01)

(58) Field of Classification Search
None
See application file for complete search history.

(56) References Cited

U.S. PATENT DOCUMENTS

| | | |
|---|---|---|
| 5,538,848 A | 7/1996 | Livak |
| 9,442,111 B2 | 9/2016 | Lindsay |
| 9,535,070 B2 | 1/2017 | Saul |
| 9,938,523 B2 | 4/2018 | Labaer |
| 2014/0371091 A1 | 12/2014 | Wiktor |
| 2016/0041159 A1 | 2/2016 | Abaer |
| 2016/0085912 A1* | 3/2016 | Jones ............... G16H 50/80 702/19 |
| 2017/0088830 A1 | 3/2017 | Labaer |
| 2017/0115299 A1 | 4/2017 | Saul |
| 2017/0176423 A1 | 6/2017 | Anderson |
| 2018/0201923 A1 | 7/2018 | Abaer |
| 2018/0267029 A1 | 9/2018 | Wiktor |
| 2019/0062728 A1 | 2/2019 | Abaer |

FOREIGN PATENT DOCUMENTS

| | | |
|---|---|---|
| WO | 2013063126 A2 | 5/2013 |
| WO | 2013090364 A1 | 6/2013 |
| WO | 2014143954 A2 | 9/2014 |
| WO | 2014145458 A1 | 9/2014 |
| WO | 2015148202 A1 | 10/2015 |
| WO | 2015175755 A1 | 11/2015 |
| WO | 2017048709 A1 | 3/2017 |
| WO | 2018156553 A1 | 8/2018 |

OTHER PUBLICATIONS

Loens, K. et al., Evaluation of NucliSens easyMAG for Automated Nucleic Acid Extraction from Various Clinical Specimens, J. Clin. Microbiol., vol. 45, pp. 421-425 (Year: 2007).*
PMA™ Real-Time PCR Bacterial Viability Kit (Biotium, pp. 1-3 (Year: 2015).*
Petersen, B.T. et al., Infection Using ERCP Endoscopes, Gastroenerol., vol. 151, pp. 46-50 (Year: 2016).*
McDonnell, G. et al., Effectiveness of the System 1E Liquid Chemical Sterilant Processing System for reprocessing duoendoscopes, Am. J. Infect. Control, vol. 44, pp. 685-688 (Year: 2016).*
Alvarez, G., et al., Method to quantify live and dead cells in multi-species oral biofilm by real-time PCR with propidium monoazide. AMB Express, 2013. 3(1): p. 1.
Bialvaei, A.Z., et al., Current methods for the identification of carbapenemases. J Chemother, 2015: p. 1973947815Y0000000063.
Doyle, D., et al., Laboratory detection of Enterobacteriaceae that produce carbapenemases. J Clin Microbiol, 2012. 60(12): p. 3877-80.
Elizaquivel, P., et al, Application of propidium monoazide quantitative PCR for selective detection of live *Escherichia coli* 0157:H7 in vegetables after inactivation by essential oils. Int J Food Microbiol, 2012. 159(2): p. 115-21.
Epstein, L., et al., New Delhi metallo-beta-lactamase-producing carbapenem-resistant *Escherichia coli* associated with exposure to duodenoscopes. JAMA, 2014. 312(14): p. 1447-55.
Findlay, J., et al. Evaluation of three commercial assays for rapid detection of genes encoding clinically relevant carbapenemases in cultured bacteria. J Antimicrob Chemother 70, 1338-42 (2015).
Gensberger, E.T., et al, Propidium monoazide-quantitative polymerase chain reaction for viable *Escherichia coli* and Pseudomonas aeruginosa detection from abundant background microflora. Anal Biochem, 2013. 441(1): p. 69-72.

(Continued)

*Primary Examiner* — Teresa E Strzelecka
(74) *Attorney, Agent, or Firm* — Quarles & Brady LLP

(57) ABSTRACT

Provided herein are qPCR-based methods for quantitatively detecting and differentiating between live and dead pathogenic bacteria such as carbapenem-resistant Enterobacteriaceae (CRE). Also provided herein are simple, fast, and reliable genomic DNA extraction methods with improved efficiency.

14 Claims, 9 Drawing Sheets

Specification includes a Sequence Listing.

(56) References Cited

OTHER PUBLICATIONS

Hammoudi, D., et al., How to detect carbapenemase producers? A literature review of phenotypic and molecular methods. J Microbiol Methods, 2014. 107: p. 106-18.

Hong, S.S., et al., Multiplex PCR for rapid detection of genes encoding class A carbapenemases. Ann Lab Med, 2012. 32(5): p. 359-61.

Kim, Y.J., et al., Evaluation of propidium monoazide real-time PCR for early detection of viable *Mycobacterium tuberculosis* in clinical respiratory specimens. Ann Lab Med, 2014. 34(3): p. 203-9.

Monteiro, J., et al., Rapid detection of carbapenemase genes by multiplex real-time PCR. J Antimicrob Chemother, 2012. 67(4): p. 906-9.

Nkuipou-Kenfack, E., et al., Improving efficiency of viability-PCR for selective detection of live cells. J Microbiol Methods, 2013. 93(1): p. 20-4.

Nocker, A. et al, Novel approaches toward preferential detection of viable cells using nucleic acid amplification techniques. FEMS Microbiol Lett, 2009. 291(2): p. 137-42.

Nocker, A. et al., "Comparison of propidium monoazide with ethidium monoazide fordifferentiation of live vs. dead bacteria by selectiveremoval of DNA from dead cells", Journal of Microbiological Methods, 2006 [available online Jun. 2006], vol. 67, pp. 310-320, (DOI:10.1016/j.mimet.2006.04.015).

Nocker, A., et al., Use of propidium monoazide for live/dead distinction in microbial ecology. Appl Environ Microbiol, 2007. 73(16): p. 5111-7.

Nogva, H.K., et al., Application of 5'-nuclease PCR for quantitative detection of Listeria monocytogenes in pure cultures, water, skim milk, and unpasteurized whole milk. Appl Environ Microbiol, 2000. 66(10): p. 4266-71.

Nogva, H.K., et al., Ethidium monoazide for DNA-based differentiation of viable and dead bacteria by 5'-nuclease PCR. Biotechniques, 2003. 34(4): p. 804-8, 810, 812-3.

Nordmann, P., et al., How to detect NDM-1 producers. J Clin Microbiol, 2011. 49(2): p. 718-21.

Pollett, S. et al. Phenotypic and molecular characteristics of carbapenem-resistant Enterobacteriaceae in a health care system in Los Angeles, California, from 2011 to 2013. J Clin Microbiol 52, 4003-9 (2014).

Rutala, W.A. et al, Gastrointestinal endoscopes: a need to shift from disinfection to sterilization? JAMA, 2014. 312 (14): p. 1405-6.

Rutala, W.A. et al. Selection of the ideal disinfectant. Infect Control Hosp Epidemiol 35, 855-65 (2014).

Rutala, W.A., et al, Microbial contamination on used surgical instruments. Infect Control Hosp Epidemiol, 2014. 35 (8): p. 1068-70.

Shin, S. et al., "Recent Update on Microbiological Monitoring of Gastrointestinal Endoscopes after High-Level Disinfection", Clinical Endoscopy, Sep. 2015, vol. 48, No. 5, pp. 369-373, (DOI:10.5946/ce.2015.48.5.369).

Soejima, T., et al., Method to Detect Only Live Bacteria during PCR Amplification. J Clin Microbiol, 2008. 46(7): p. 2305-13.

ThermoFisher Scientific, TAQMAN Gene Expression Assay Solutions Brochure, 11 pages, accessed online at [http://tools.thermofisher.com/content/sfs/brochures/taqman-gex-brochure.pdf] on Jul. 8, 2019.

Van Frankenhuyzen, J.K., et al., Molecular pathogen detection in biosolids with a focus on quantitative PCR using propidium monoazide for viable cell enumeration. J Microbiol Methods, 2011. 87(3): p. 263-72.

Wang, L. and et al, EMA-real-time PCR as a reliable method for detection of viable *Salmonella* in chicken and eggs. J Food Sci, 2010. 75(3): p. M134-9.

Wang, L., et al, A rapid low-cost real-time PCR for the detection of Klebsiella pneumonia carbapenemase genes. Ann Clin Microbiol Antimicrob, 2012. 11: p. 9.

Buck, G.A. et al., Design Strategies and Performance of Custom DNA Sequencing Primers, Biotechniques, vol. 27, pp. 528-536 (Year: 1999).

Cunningham, S.A. et al., Rapid and Simultaneous Detection of Genes Encoding Klebsiella pneumoniae Carbapenemase (blaKPC) and New Delhi Metallo-beta-Lactamase (blaNDM) in Gram-Negative Bacilli, J. Clin. Microbiol., vol. 51, pp. 1269-1271 (Year: 2013).

GENBANK Accession No. JF431298, Klebsiella pneumoniae strain NF10-8085 class A carbapenemase blaKPC-2 (blaKPC-2) gene, partial cds (Year: 2016).

Kola, A. et al., An outbreak of carbapenem-resistant OXA-48-producing Klebsiella pneumonia associated to duodenoscopy, Antimicrobial Resist. Infect. Control, vol. 4:8, pp. 1-4 (Year: 2015).

Lerner, A. et al., Rectal Swabs are Suitable for Quantifying the Carriage Load of KPC-ProducingCarbapenem-Resistant Enterobacteriaceae, Antimicrob. Agents Chem., vol. 57, pp. 1474-1479 (Year: 2013).

Li, D. et al., Quantification of viable bacteria in wastewater treatment plants by using propidium monoazide combined with quantitative PCR (PMA-qPCR), J. Environ. Sci., vol. 26, pp. 299-306 (Year: 2014).

Marsh, J. W. et al., Genomic Epidemiology of an Endoscope-Associated Outbreak of Klebsiella pneumoniae Carbapenemase (KPC)-Producing K. pneumoniaePLOS One, vol. 10(12): e0144310, pp. 1-18 (Year: 2015).

Nocker, A. et al., Molecular monitoring of disinfection efficacy using propidium monoazide in combination with quantitative PCR, J. Microbiol. Meth., vol. 70, pp. 252-260 (Year: 2007).

Pollett, S. et al., Phenotypic and Molecular Characteristics of Carbapenem-Resistant Enterobacteriaceae in a Health Care System in Los Angeles, California, from 2011 to 2013, J. Clin. Microbiol., vol. 52, pp. 4003-4009 (Year: 2014).

Pollett, S. et al., Phenotypic and Molecular Characteristics of Carbapenem-Resistant Enterobacteriaceae in a Health Care System in Los Angeles, California, from 2011 to 2013, J. Clin. Microbiol., vol. 52, supplemental Table 1 (Year: 2014).

Van Der Zee, A. et al., Multi-centre evaluation of real-time multiplex PCR for detection of carbapenemase genes OXA-48, VIM, IMP, NDM and KPC, BMC Infectious Dis., vol. 14:27, pp. 1-5 (Year: 2014).

Van Der Zee, A. et al., Multi-centre evaluation of real-time multiplex PCR for detection of carbapenemase genes OXA-48, VIM, IMP, NDM and KPC, BMC Infectious Dis., vol. 14:27, supplemental Table S1 (Year: 2014).

\* cited by examiner

| Sample ID | NDM1 | | | |
|---|---|---|---|---|
| | Ct Mean | Average Ct | Ct SD | Average SD |
| 100% Live | 11 | 10.8 | 0.341 | 0.421 |
| 100% Live | 10.3 | | 0.319 | |
| 100% Live | 10.9 | | 0.245 | |
| 100% Dead | 27.2 | 28.3 | 0.444 | 1.526 |
| 100% Dead | 28 | | 0.873 | |
| 100% Dead | 29.7 | | 1.821 | |
| 10% Live + 90% Dead | 14.5 | 14.4 | 0.29 | 0.196 |
| 10% Live + 90% Dead | 14.3 | | 0.135 | |
| 10% Live + 90% Dead | 14.4 | | 0.101 | |
| PBS | ND | | ND | |

METHODS FOR DETECTION AND QUANTIFICATION OF INFECTIOUS CARBAPENEM RESISTANT ENTEROBACTERIACEAE (CRE)

CROSS-REFERENCE TO RELATED APPLICATIONS

This application is a continuation of U.S. application Ser. No. 16/172,379 filed on Oct. 26, 2018 and published as U.S. 2019/0127778, and which claims priority to U.S. Provisional Patent Application No. 62/577,359, filed Oct. 26, 2017. Both applications are incorporated herein by reference as if set forth in their entireties.

REFERENCE TO A SEQUENCE LISTING SUBMITTED VIA EFS-WEB

This application includes an electronically submitted Sequence Listing in .txt format. The .txt file contains a sequence listing entitled "112624_01027_ST25.TXT" and was created on Jun. 11, 2021, and is 1,535 bytes in size. The Sequence Listing contained in this .txt file is part of the specification and is hereby incorporated herein in its entirety.

BACKGROUND

Nosocomial infections of Carbapenem-resistant Enterobacteriaceae (CRE) have been reported in several healthcare facilities across United States. In particular, there have been multiple reports of CRE transmission through duodenoscopes in patients undergoing endoscopic retrograde cholangiopancreatography (ERCP). Treatment options for CRE nosocomial infections are limited, and invasive infections are associated with a high mortality rate. This is a substantial public health concern as approximately 500,000 ERCPs are performed annually in the US. Since the reporting of these outbreaks, the FDA has recommended additional chemical sterilization techniques such as ethylene oxide sterilization or microbiological surveillance culture, and many endoscopy units have started routinely screening patients and/or duodenoscopes for CRE. Monitoring endoscope disinfection through culture is labor-intensive, time consuming, and prone to false positives due to non-pathogenic environmental contaminants. Sterilization techniques are expensive and they are not available at most endoscopy units. Without advancements in endoscope design or reprocessing techniques, the risk of persistent contamination and transmission will continue to be a significant public health concern. Accordingly, there remains a need in the art for improved, reliable, real-time monitoring methods for detection of live pathogens on medical devices such as endoscopes.

SUMMARY OF THE DISCLOSURE

In a first aspect, provided herein is a method of detecting live and dead carbapenem-resistant Enterobacteriaceae (CRE) in a sample comprising bacteria, the method comprising: (a) incubating the sample in the presence of a DNA intercalating dye that selectively permeates into dead bacterial cells, wherein incubating comprises contacting the DNA intercalating dye to the sample for about 10 minutes and exposing the contacted sample to light for about 15 minutes to obtain a light-treated, dye-treated sample; (b) extracting genomic DNA (gDNA) from bacteria of the light-treated, dye-treated sample; (c) pre-amplifying the extracted genomic DNA, wherein pre-amplifying comprises performing 8 to 12 cycles of target-specific limited amplification using a pair of CRE-specific oligonucleotide primers selected from the group consisting of SEQ ID NO:1, SEQ ID NO:2, SEQ ID NO:3, and SEQ ID NO:4; (d) performing a real-time PCR reaction to amplify nucleic acids of the extracted gDNA, wherein performing comprises providing the pair of CRE-specific oligonucleotide primers and a fluorescently labeled oligonucleotide probe to the extracted gDNA; and (e) determining a threshold cycle value (Ct value) and comparing the Ct value to a standard obtained by quantitative real-time PCR of known quantities of DNA of live and dead bacteria to detect live and dead bacteria in the sample. The DNA intercalating dye can be propidium monoazide (PMA™) or ethidium monoazide (EMA). Extracting gDNA can comprise contacting the sample to water and boiling the contacted sample at 100° C. for about 15 to about 25 minutes. Extracting gDNA can comprise contacting the sample to a cell lysis solution. The method can further comprise quantifying live and dead CRE detected in the sample. The sample can be a medical device-derived sample. The medical device can be a duodenoscope. The sample can be obtained by swabbing the medical device. The sample can be a patient-derived sample.

In another aspect, provided herein is a genomic DNA (gDNA) extraction method, where the method comprises resuspending a sample containing or suspected of containing bacteria in water; and boiling the resuspended sample at 100° C. for about 15 to about 25 minutes.

In a further aspect, provided herein is a method for real-time monitoring for live carbapenem-resistant Enterobacteriaceae (CRE) on a medical device, where the method comprises (a) contacting the medical device to an elution buffer comprising a DNA intercalating dye; (b) exposing the contacted medical device to light; (c) collecting the device-contacted elution buffer; (d) centrifuging the collected buffer to form a pellet of any live or dead bacteria eluted from the medical device; (e) resuspending the pellet to form a suspension; (f) extracting DNA from any live or dead bacteria in the suspension; and (g) performing quantitative real-time PCR using at least two CRE-specific oligonucleotide primers selected from the group consisting of SEQ ID NO:1, SEQ ID NO:2, SEQ ID NO:3, and SEQ ID NO:4 and a fluorescently labeled oligonucleotide probe, wherein the presence of live CRE on the medical device is detected by comparing amplified nucleic acids to a standard curve obtained by quantitative real-time PCR of known quantities of DNA of the live CRE. The incubating step can comprise contacting the DNA intercalating dye and an enhancer to the sample. The medical device can be a duodenoscope. The sample can be obtained by swabbing the medical device.

In another aspect, provided herein is a method for rapidly screening for live carbapenem-resistant Enterobacteriaceae (CRE) in a patient sample prior to the patient being subject to an endoscopic retrograde cholangiopancreatography (ERCP), where the method comprises: (a) contacting a sample from the patient to a DNA intercalating dye; (b) exposing the contacted sample to light; (c) collecting the light exposed, contacted sample; (d) extracting genomic DNA from any bacteria in the suspension; and (e) performing quantitative real-time PCR using a set of CRE-specific oligonucleotide primers and a labeling probe, wherein the presence of live CRE is detected by comparing amplified nucleic acids to a standard curve obtaining by quantitative real-time PCR of known quantities of DNA of live CRE; wherein, if the patient sample is negative for live CRE, the duodenoscope used for the patient's ERCP is not selected for chemical sterilization, and wherein, if the patient sample is positive for live CRE, the duodenoscope is selected for chemical sterilization. The sample can be a rectal swab.

INCORPORATION BY REFERENCE

Figures 1A, 1B:
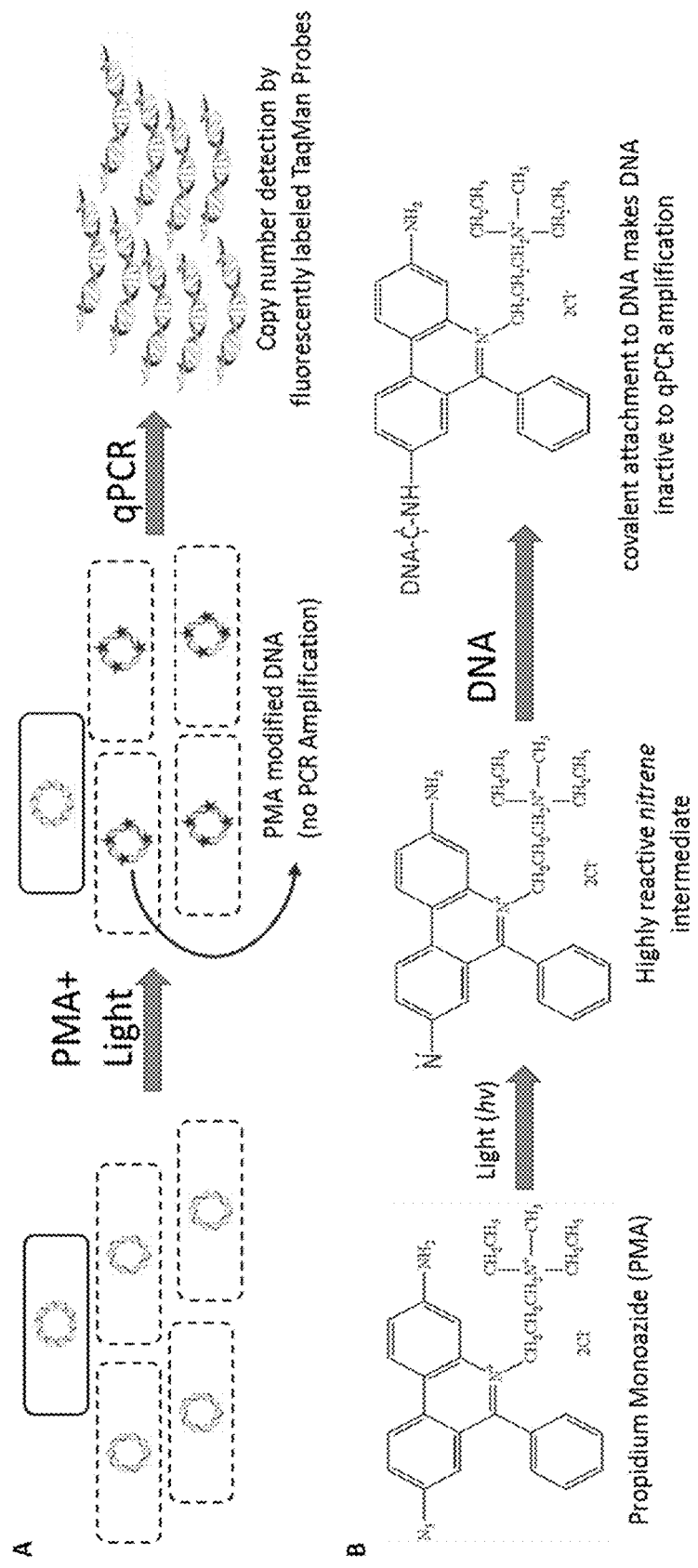
FIGS. 1A-1B. (A) Live cell membrane-impermeable propidium monoazide (PMA) dye selectively enters dead cells and covalently modifies DNA in the presence of bright light. (B) PMA-modified DNA cannot be amplified by qPCR.

All publications, patents, and patent applications mentioned in this specification are herein incorporated by reference to the same extent as if each individual publication, patent, and patent application was specifically and individually indicated to be incorporated by reference.

DETAILED DESCRIPTION

The methods and systems provided herein are based at least in part on the inventors' development of qPCR-based protocols for screening duodenoscopes for the presence of live or dead carbapenem-resistant Enterobacteriaceae (CRE). In particular, the inventors developed rapid qPCR-based diagnostic tests to detect, discriminate, and quantify live CRE in a sample (e.g., swab of a duodenoscope) within a few hours of sample acquisition. By integrating such protocols with an improved method for genomic DNA (gDNA) extraction, the technology described herein provides an efficient and reproducible platform to quantitatively detect and differentiate CREs and, accordingly, rapidly and reliably identify duodenoscopes that harbor carbapenem-resistant Enterobacteriaceae (CRE) and pose a risk to subsequent endoscopic retrograde cholangiopancreatography (ERCP) patients.

There is no standard qPCR-based technology to detect and differentiate live versus dead CREs in clinical specimens. Currently existing qPCR assays detect CREs but do not distinguishes the detected nucleic acids from "leftover" DNA of dead cells in the specimen. Our technology identifies live, potentially harmful bacteria that can lead to unwanted nosocomial infections. Advantages of the methods and systems provided herein include the ability to produce reliable, reproducible results within about 2-3 hours of sampling and to enrich, detect, and quantify only live pathogens in a sample. The methods and systems provided herein will be particularly beneficial to institutions or clinical practices that do not have ready access to reference laboratories or chemical sterilization facilities. Without being bound to any particular theory or mechanism of action, it is believed that DNA intercalating agents like propidium monoazide (PMA™, Biotium) can selectively permeate dead cells and render their DNA unusable for polymerase chain reaction (PCR) amplification, thereby selectively enriching for quantitative polymerase chain reaction (qPCR)-capable DNA template from living pathogens that can be quantified using a real-time PCR assay such as, for example, a TaqMan® (Applied Biosystems™) gene expression assay.

In a first aspect, provided herein is a method for detecting about 5 to about 9 logs of a pathogen (e.g., pathogenic bacteria) in a sample. In certain embodiments, the method to detect and quantify live and dead bacteria of a particular category in a sample comprising bacteria comprises: (a) incubating the sample in question with a DNA intercalating dye that selectively permeates into dead bacterial cells, wherein incubating comprises contacting the DNA intercalating dye to the gDNA and exposing the contacted gDNA to light for about 15 minutes to obtain a light-treated gDNA/dye sample; (b) extracting genomic DNA (gDNA) from bacteria of the sample; (c) pre-amplifying the extracted genomic DNA wherein pre-amplifying comprises 8-12 cycles of target-specific limited amplification using at least two pathogen-specific oligonucleotide primers; (e) performing a real-time PCR reaction to amplify nucleic acids of the light-exposed gDNA, wherein performing comprises providing the pair of pathogen-specific oligonucleotide primers and a labeling probe to the light-treated gDNA/dye sample; and (f) determining a threshold cycle value (Ct value) and comparing the Ct value to a standard obtained by quantitative real-time PCR of known quantities of DNA of the live and dead bacteria. In some cases, the pathogenic bacteria are CRE and the least two primers are CRE-specific oligonucleotide primers selected from the group consisting of SEQ ID NO:1, SEQ ID NO:2, SEQ ID NO:3, and SEQ ID NO:4. In certain embodiments, PreAmp MasterMix (product of Applied Biosystems, Inc.) is used for the pre-amplifying step.

Real-time PCR can amplify DNA or the like to several hundred thousand-fold by continuously performing amplification cycles of "thermal denaturation→annealing with a primer→polymerase extension reaction." Real-time PCR monitors the resulting amplification products in real time to perform a quantitative assay of the trace nucleic acids. In certain embodiments, the gene expression assay is a "TaqMan® probe" method (product of Applied Biosystems, Inc.), which uses as a probe an oligonucleotide modified at the 5' terminal with a fluorescent material and at the 3' terminal with a quencher material. TaqMan® PCR is a method of detecting and quantifying the presence of a DNA sequence. Briefly, a FRET oligonucleotide probe is designed that it overlaps a target sequence of interest. The FRET probe and PCR primers (at least one upstream and at least one downstream of the target sequence of interest) are cycled in the presence of a thermostable polymerase and dNTPs.

In some cases, the method further comprises a pre-amplification step to increase the limit of detection (sensitivity). For example, 8 to 12 pre-amplification cycles can be added to increase the sensitivity of qPCR-based assays that are not sufficiently sensitive to detect at least 1-10 live bacteria.

In some cases, the DNA intercalating dye (also known as a nucleic acid intercalating moiety) is contacted to the sample for incubated for sufficient time for the dye to non-covalently bind and intercalate in the nucleic acid. For example, the dye and nucleic acid may be incubated for at least 5 minutes and usually not more than about 2 hours, where complex formation will normally be complete in less than about one hour, usually in fewer than 30 minutes at room temperature. In some cases, the DNA intercalating dye is contacted to the sample for a length of time between about 5 minutes to about 120 minutes (e.g., about 5, 10, 15, 20, 25, 30 35, 40, 45, 50, 55, 60, 65, 70, 75, 80, 85, 90, 95, 100, 105, 110, 150, 120 minutes, inclusive). Preferably, the DNA intercalating dye is contacted to the sample for about 5 to about 30 minutes. More preferably, the DNA intercalating dye is contacted to the sample for about 10 minutes. In some cases, contacting of the sample and DNA intercalating dye are brought together in an appropriately buffered medium.

The term "labeling probe" generally, according to various embodiments, refers to a molecule used in an amplification reaction, typically for quantitative or qPCR analysis, as well as end-point analysis. Such labeling probes may be used to monitor the amplification of the target polynucleotide. In some embodiments, fluorescently labeled oligonucleotide probes present in an amplification reaction are suitable for monitoring the amount of amplicon(s) produced as a function of time. Such fluorescently labeled oligonucleotide probes include, but are not limited to, the 5'-exonuclease assay TaqMan® labeling probes described herein (see also U.S. Pat. No. 5,538,848). While TaqMan® assays and reagents are used to demonstrate the features of embodiments of the methods described herein, one of ordinary skill in the art will recognize that a variety of assays including probe reagents may be utilized to produce data that may be analyzed according to various embodiments of the methods provided herein.

In some cases, the method also comprises, as a first step, performing PCR using as templates serially-diluted standard samples the concentrations of which are known. Numbers of cycles (threshold cycles: Ct values) required to each a certain constant amount of amplification product are then determined. A calibration line is then prepared by plotting these Ct values and initial DNA amounts along the abscissa and the ordinate, respectively. The amount of target DNA in the sample can be determined using this Ct value and the above-mentioned calibration line. In a real-time PCR reaction, dead cell DNA will show delayed amplification and higher Ct than live cells. In a mixed population, qPCR permits quantitation of viable bacteria in the sample.

Preferably, the DNA intercalating dye is cell membrane-impermeable and thus can be used to selectively modify DNA from dead cells with compromised membrane integrity, while leaving DNA from viable cells intact. In some cases, the DNA intercalating agent is PMA™ (Biotium). PMA™ is a high affinity photoreactive DNA binding dye useful in the selective detection of viable pathogenic cells by quantitative real-time PCR. In some cases, genomic DNA is contacted to PMA™, or to PMA plus a PMA™ enhancer, which improves PMA™- and PMAxx™ (Biotium)-mediated discrimination between live and dead gram-negative bacteria. Referring to FIGS. 1A and 1B, when a double-stranded DNA-PMA complex is photoactivated by exposure to light (e.g., visible light), the monoazide group of PMA is converted to a highly reactive nitrene radical which readily reacts with any hydrocarbon moiety to form a stable covalent bond (see FIG. 1B), and prevents its use as a template for PCR. In other cases, the DNA intercalating dye is ethidium monoazide (EMA). Preferably, photoactivation of the DNA intercalating dye occurs open exposure to one or more sources of light (e.g., visible light) which emits light having a wavelength ranging from 350 to 1100 nm. Appropriate light sources include, without limitation, a light emitting diode (LED), laser, incandescent lamp, and halogen light. In some cases, the light source is one or more LEDs having an output wavelength of about 465 nm to about 475 nm.

In some cases, it may be advantageous for the methods of this disclosure to include a centrifugation step. For example, it may be advantageous to use centrifugation to enrich for live and dead pathogens when screening a sample for the presence of pathogens. Live and dead bacteria can be enriched by centrifugation at 5000×g for about 5 to about 20 minutes. In some case, centrifugation is at 5000× g for about 10 to about 15 minutes. Pelleted bacteria can be lysed in an appropriate buffer to facilitate DNA extraction. In some cases, extracted DNA will be subjected to qPCR amplification to quantify the number of live bacteria from the sample.

As used herein the term "pathogen" refers to an organism, including a microorganism, which causes disease in another organism (e.g., animals and plants) by directly infecting the other organism, or by producing agents that causes disease in another organism (e.g., bacteria that produce pathogenic toxins and the like). As used herein, pathogens include, but are not limited to bacteria, protozoa, fungi, parasites, viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms which may not ordinarily be pathogenic in a non-immunocompromised host. In some cases, pathogens detected by the method comprise one or more clinically relevant species of bacteria, virus, fungus, *mycoplasma*, or parasite.

In some cases, the pathogens are gram negative bacteria, a group which encompasses cocci, nonsporulating rods, and sporulating rods. Gram-negative bacteria include without limitation Enterobacteriaceae, Carbapenem-resistant Enterobacteriaceae (CRE), *Pseudomonas aeruginosa, Stenotrophomonas maltophilia, Burkholderia cepacia,*

*Alcaligenes xylosoxidans, Acinetobacter, Haemophilus, Neisseria* species, *Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis,* and *Chlamydia trachomatis.* In certain embodiments, the methods detect Carbapenem-resistant Enterobacteriaceae (CRE) in a sample.

In certain embodiments, the method comprises subjecting a PMA- and light-treated sample to 5' nuclease-based real-time PCR amplification using pathogenic specific oligonucleotide primers and a qPCR probe.

Samples appropriate for the methods provided herein include clinical specimens (diagnostic samples collected as part of standard clinical procedures) and samples obtained by swabbing or otherwise sampling a medical device.

In another aspect, provided herein is a system that integrates the above-described elements for quantitative detection and differentiation of live versus dead CRE in a sample.

It will be advantageous in some embodiments to apply Clinical Laboratory Standards Institute (CLSI) guidelines (EP17-A2) to calculate Limit of Blank (LoB), Limit of Detection (LoD) and Limit of Quantification (LoQ) for each assay and to determine false positive and false negative rates for each of the assays within the detectable range. LoB is the highest measurement result that is likely to be observed for a blank. LoD is the lowest number of DNA copies that can be detected, perhaps not quantified. LoQ is the lowest number of DNA copies in the sample that can be quantified with acceptable precision under the stated experimental condition. Determining the LOB, LoD, and LoQ helps to define the detection capabilities and limitations of a particular assay.

In a further aspect, provided herein is a simple, fast, and reliable genomic DNA (gDNA) extraction method. In some embodiments of the extraction method, cells are re-suspended in water and boiled at 100° C. for about 20-30 minutes. No other processing required before quantification. As described herein and the Examples that follow, the gDNA extraction methods facilitate maximum DNA extraction with >90% efficiency relative to commercially available DNA extraction methods.

Figures 8A, 8B:
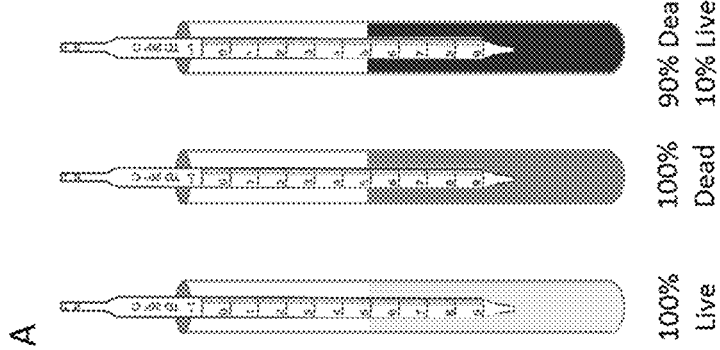
FIGS. 8A-8B illustrate an exemplary serological pipet-dip test to mimic sampling from soiled or processed duodenoscopes. (A) Same number of cultured live, dead, and mixed CREs were taken in to three 15 mL conical tubes. Serological pipets were dipped in to CREs to the depth of 5 mL and retrieved to extract bacterial cells by washing pipettes in phosphate buffered saline (PBS). (B). Collected cells were exposed to PMA treatment before extracting DNA for live/dead quantification by qPCR.

In a further aspect, provided herein is a method for real-time monitoring for live pathogenic bacteria on a medical device (e.g., duodenoscope), wherein the method comprises (a) contacting the medical device to an elution buffer comprising a DNA intercalating dye; (b) exposing the contacted medical device to light; (c) collecting the device-contacted elution buffer; (d) centrifuging the collected buffer to form a pellet of any live or dead bacteria eluted from the medical device; (e) resuspending the pellet to form a suspension; (f) adding a cell lysis solution to the suspension to extract DNA from any lysed live or dead bacteria in the suspension; and (g) performing quantitative real-time PCR using a set of pathogen-specific oligonucleotide primers and a labeling probe, wherein the presence of live pathogenic bacteria on the medical device is detected by comparing amplified nucleic acids to a standard curve obtained by quantitative real-time PCR of known quantities of DNA of the pathogenic bacteria. An exemplary sampling protocol is illustrated in FIGS. 8A-8B. In some cases, the live pathogenic bacteria comprise one or more clinically relevant species such as Carbapenem-resistant Enterobacteriaceae (CRE) or another gram-negative bacteria species. The sample can be obtained by swabbing the medical device. In some cases, the medical device is a duodenoscope. In such cases, sample collection can be performed according to the Federal Drug Administration's interim duodenoscope sampling method guidelines or a variation of such guidelines. Samples that are important to obtain include, without limitation, the Instrument Channel Flush and submerged distal end and elevator mechanism sample. In some cases, the elution buffer is the FDA recommended elution buffer: phosphate buffered saline (PBS) with 0.02% Tween-20.

In another aspect, provided herein is a method for rapidly screening for live Carbapenem-resistant Enterobacteriaceae (CRE) in a patient sample prior to the patient being subject to an endoscopic retrograde cholangiopancreatography (ERCP). The method can comprise (a) contacting a sample from the patient to a DNA intercalating dye; (b) exposing the contacted sample to light; (c) collecting the light exposed, contacted sample; (d) adding a cell lysis solution to the sample of (c) to extract DNA from any lysed live or dead bacteria in the suspension; and (e) performing quantitative real-time PCR using a set of CRE-specific oligonucleotide primers and a labeling probe, wherein the presence of live CRE is detected by comparing amplified nucleic acids to a standard curve obtaining by quantitative real-time PCR of known quantities of DNA of live CRE; wherein, if the patient sample is negative for live CRE, the duodenoscope used for the patient's ERCP is not selected for chemical sterilization, and wherein, if the patient sample is positive for live CRE, the duodenoscope is selected for chemical sterilization. In some cases, the sample is a rectal swab.

In another aspect, provided herein is an article of manufacture such as a kit comprising components useful for quantitative detection and differentiation of live versus dead CRE in a sample according to the methods provided herein. In some cases, the kit comprises one or more of a DNA intercalating dye, pathogen-specific primers, a lysis buffer, sampling materials (e.g., swabs, elution buffer), and instructions for using the same to detect and differentiate, and quantify live versus dead CRE in a sample.

So that the methods and systems provided herein may more readily be understood, certain terms are defined:

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "about" means within 5% of a stated concentration range, density, temperature, or time frame.

As used herein, the term "amplified product" refers to polynucleotides that are copies of a particular polynucleotide, produced in an amplification reaction. An "amplified product," according to the invention, may be DNA or RNA, and it may be double-stranded or single-stranded. An amplified product is also referred to herein as an "amplicon".

As used herein, "subject" means any individual, which is a human, a non-human animal, any mammal, or any vertebrate. The term is interchangeable with "patient," "recipient" and "donor." A subject can be any mammalian species alive or dead.

Although the embodiments are described in considerable detail with reference to certain methods and materials, one skilled in the art will appreciate that the disclosure herein can be practiced by other than the described embodiments, which have been presented for purposes of illustration and not of limitation. Therefore, the scope of the appended claims should not be limited to the description of the embodiments contained herein.

EXAMPLES

Nosocomial infections with CRE have been reported in several healthcare facilities across United States. Treatment options are limited and invasive infections are associated with a high mortality rate. In United States, there have been multiple reports of CRE transmission through duodenoscopes in patients undergoing endoscopic retrograde cholangiopancreatography (ERCP). This is a substantial public health concern as approximately 500,000 ERCPs are performed annually in the United States. Since the reporting of these outbreaks, many endoscopy units have started routinely screening patients and/or duodenoscopes for CRE. Currently at Mayo Clinic Arizona (MCA), a rectal swab is obtained on all patients and sent to the MCR reference laboratory for a polymerase chain reaction (PCR)-based test. Turnaround time for results of this assay is usually 48-72 hours. Duodenoscopes are sequestered for this time, which places a substantial time and financial burden on the clinic. Clinical laboratories do not perform duodenoscope cultures. Furthermore, cultures from reprocessed duodenoscopes do not detect all bacteria and any viruses or parasites. In discussion with clinicians at MCA, we identified developing and validating real-time monitoring methods to assess the risk of infection as a critical unmet need.

PCR amplification from $bla_{KPC}$, $bla_{NDM-1}$ and 16sRNA has been previously reported to detect CRE in clinical samples. Based on literature, we selected three independent target sequences of 16S rRNA, *Klebsiella pneumonia* carbapenemenase (KPC), and New Delhi metallo β-lactamase (NDM1) to design and order custom TaqMan assays from Applied Biosystems. We ordered three TaqMan assays each for NDM1 and KPC, and ordered one TaqMan assay using a previously published sequence for CRE 16S rRNA. All TaqMan assays were tested for their ability to amplify using 8-logs of genomic DNA (~$2\times10^9$ to <1 molecules) as a starting template. Primer sequences are presented in Table 1. Our process included 10 cycles preamplification of templates using PreAmplification MasterMix from Thermo Fisher Scientific. Preamplification improves the sensitivity of detection and provides extremely high correlation between amplified and unamplified cDNA. The best performing assay was selected based on its ability to 1) Perform linear PCR reaction over seven-log range of input DNA template using eight to 10 fold dilutions (when Ct is plotted against $log_{10}$ input template quantity, R2 value≥0.98); 2) Detect ≥10 copies of the target; 3) Exhibit 100%±10% amplification efficiency when tested over five orders of magnitude of input template; 4) No detectable PCR amplification (Ct value>37) when there is no template added (No template control-NTC) (Table 2). NDM1 and KPC1 assays were able to detect >10 copies of genomic DNA compared to 16S rRNA probe was able to detect <1 copies of genomic DNA. It is important to note that multiple copies of 16S rRNA sequences are present within the genome.

We used TaqMan™ assay chemistry for the detection of PCR products. We note that the TaqMan™ assay is proprietary for Thermo Fisher Scientific, so the actual TaqMan™ probe sequence is unknown.

TABLE 1

Primer sequences

| Gene Name | Assay ID | Forward Primer (5'-3') | Reverse Primer (5'-3') |
|---|---|---|---|
| NDM1 | AIFATXV | GACAAGATGGGCGGTATGGA (SEQ ID NO: 1) | CTGGTTCGACAACGCATTGG (SEQ ID NO: 2) |
| KPC1 | AID1VRN | CGCCGCCAATTTGTTGCT (SEQ ID NO: 3) | GCCGATAGAGCGCATGAAG (SEQ ID NO: 4) |
| 16S | AILJKSZ | TGGAGCATGTGGTTTAATTCGA (SEQ ID NO: 5) | TGCGGGACTTAACCCAACA (SEQ ID NO: 6) |

After exploring many different DNA extraction methods, we modified an in-vitro diagnostics (IVD)-approved DNA extraction method recommended by Qiagen (QIAamp DSP DNA Mini Kit, IVD; Cat #61304) to develop a method for specific extraction of DNA from CRE. This process takes >30 minutes of DNA extraction time.

Detection and Quantification of Live vs Dead CRE: Detection and discrimination of live and dead CRE is based on our hypothesis that DNA intercalating agents like propidium monoazide (PMA) can selectively permeate dead cells and rendering their DNA inept for PCR amplification, thereby selectively enriching a live, qPCR-capable DNA template that can be quantified using TaqMan™ assays (FIG. 1). We varied PMA incubation time and concentration, which is extremely important for differentiating live and dead bacteria by using live and heat killed CRE. The amount of time and temperature necessary to generate heat-killed bacteria that yields PCR quantifiable genomic DNA was also modified to be <30 min at 100° C. PMA concentration and incubation time was selected based on maximum Ct difference that is observed between live and heat killed CRE. PMA concentration at 50 µM, with 15 minute exposure to light showed maximum difference in Ct values. We included an addition of enhancer solution that helps in differentiating live versus dead cells. PMA enhancer for gram negative bacteria was designed to improve PMA-mediated discrimination between live and dead gram-negative bacteria. When CRE bacterial DNA is amplified by PCR, samples pretreated with Enhancer show a decrease in the signal from dead cells, with no change in the signal from live cells.

Figure 2:
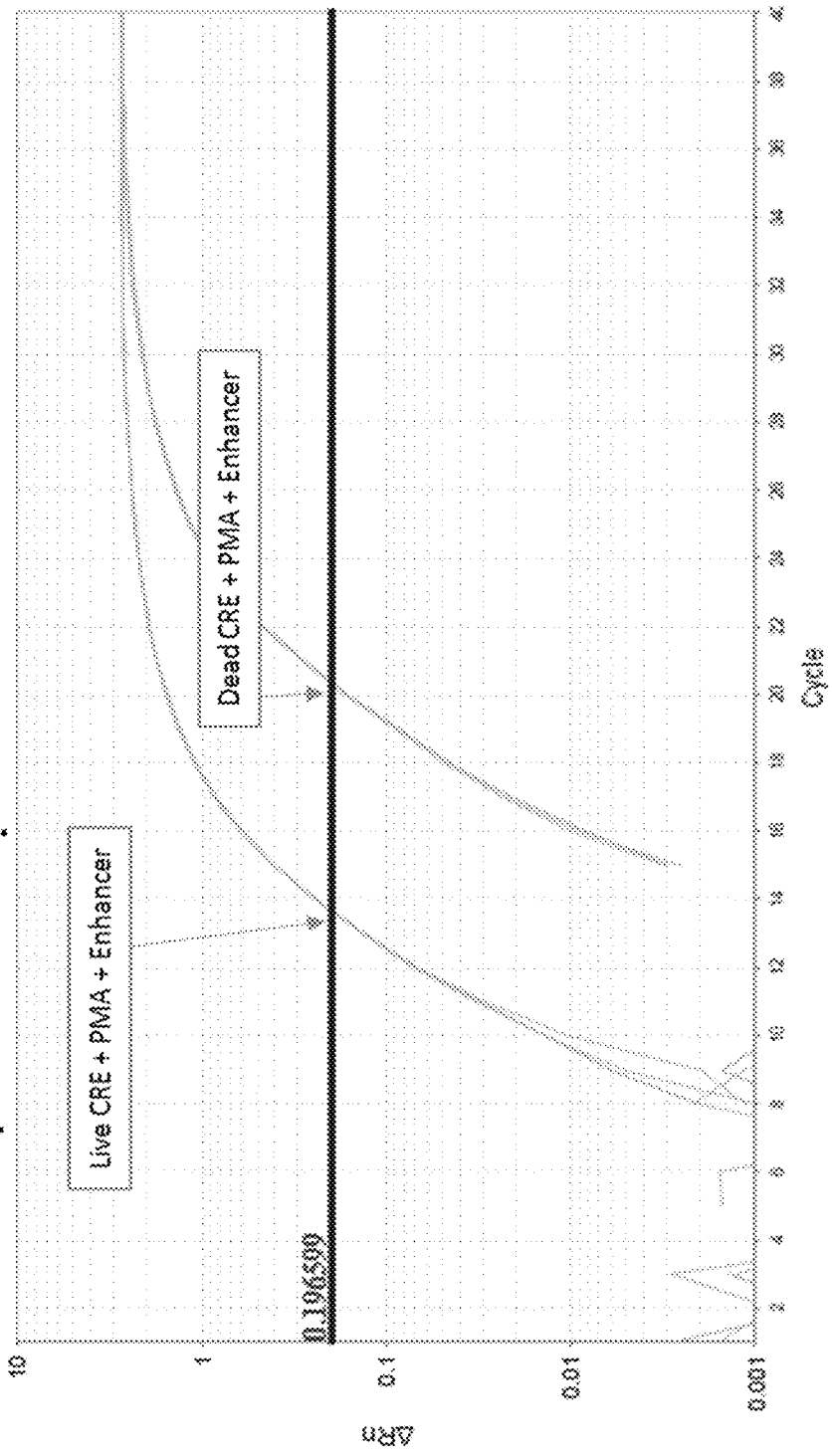
FIG. 2 presents amplification plots demonstrating the ability to discriminate between live vs dead CRE using PMA and Enhancer. 100 µL of cultured live (100%) and heat killed (100%) CRE were incubated with either 50 µM of PMA or 50 µM PMA plus 1× concentration of enhancer for 10 minutes. Samples were exposed to light for 15 minutes before DNA extraction for qPCR analysis for NDM1. Larger Ct values reflect samples containing DNA that was not amenable for qPCR amplification due to PMA and enhancer.
Figure 3:
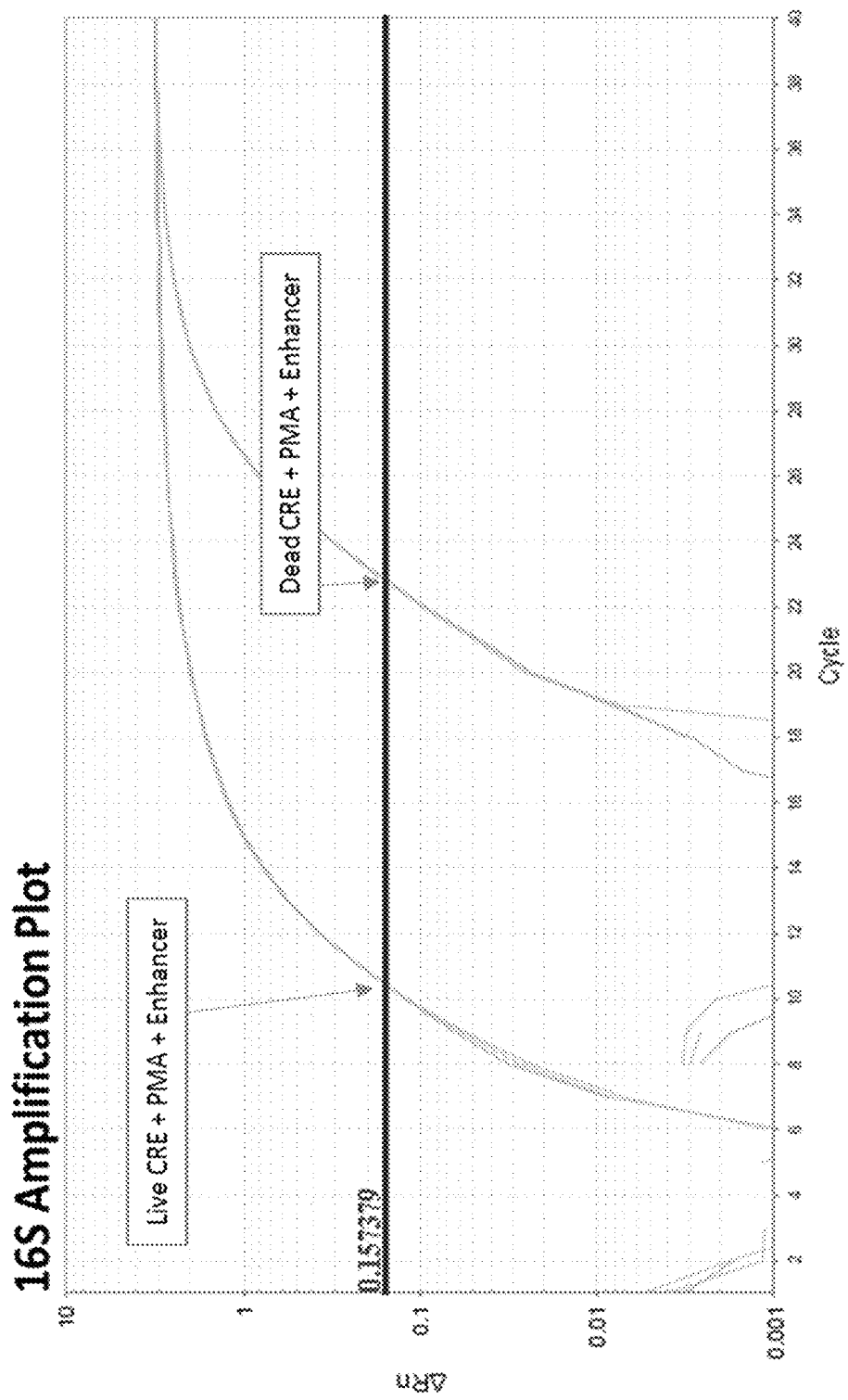
FIG. 3 presents amplification plots demonstrating the ability to discriminate between live vs dead CRE using PMA and Enhancer. 100 µL of cultured live (100%) and heat killed (100%) CRE were incubated with either 50 µM of PMA or 50 µM PMA plus 1× concentration of enhancer for 10 minutes. Samples were exposed to light for 15 minutes before DNA extraction for qPCR analysis for 16S rRNA. Larger Ct values reflect samples containing DNA that was not amenable for qPCR amplification due to PMA and enhancer.

After modifying the concentration and incubation time of PMA and Biotium PMA enhancer, we tested the ability to detect and quantify the number of CRE (FIG. 2, FIG. 3, and Table 3).

Figure 4:
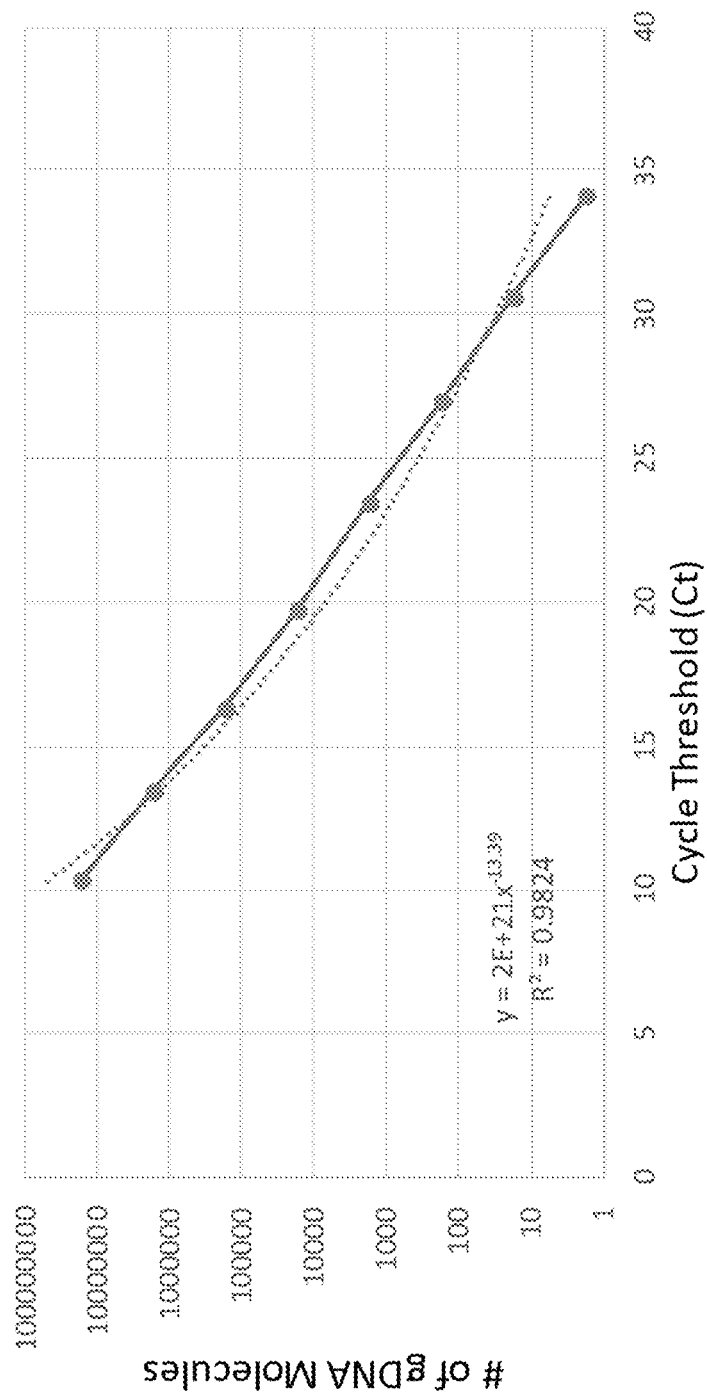
FIG. 4 demonstrates standard curves generated using known amounts of qPCR-amplified genomic DNA. CT values obtained using PMA treated and un-treated samples were used to calculate the number of molecules detected by qPCR amplification.
Figure 5:
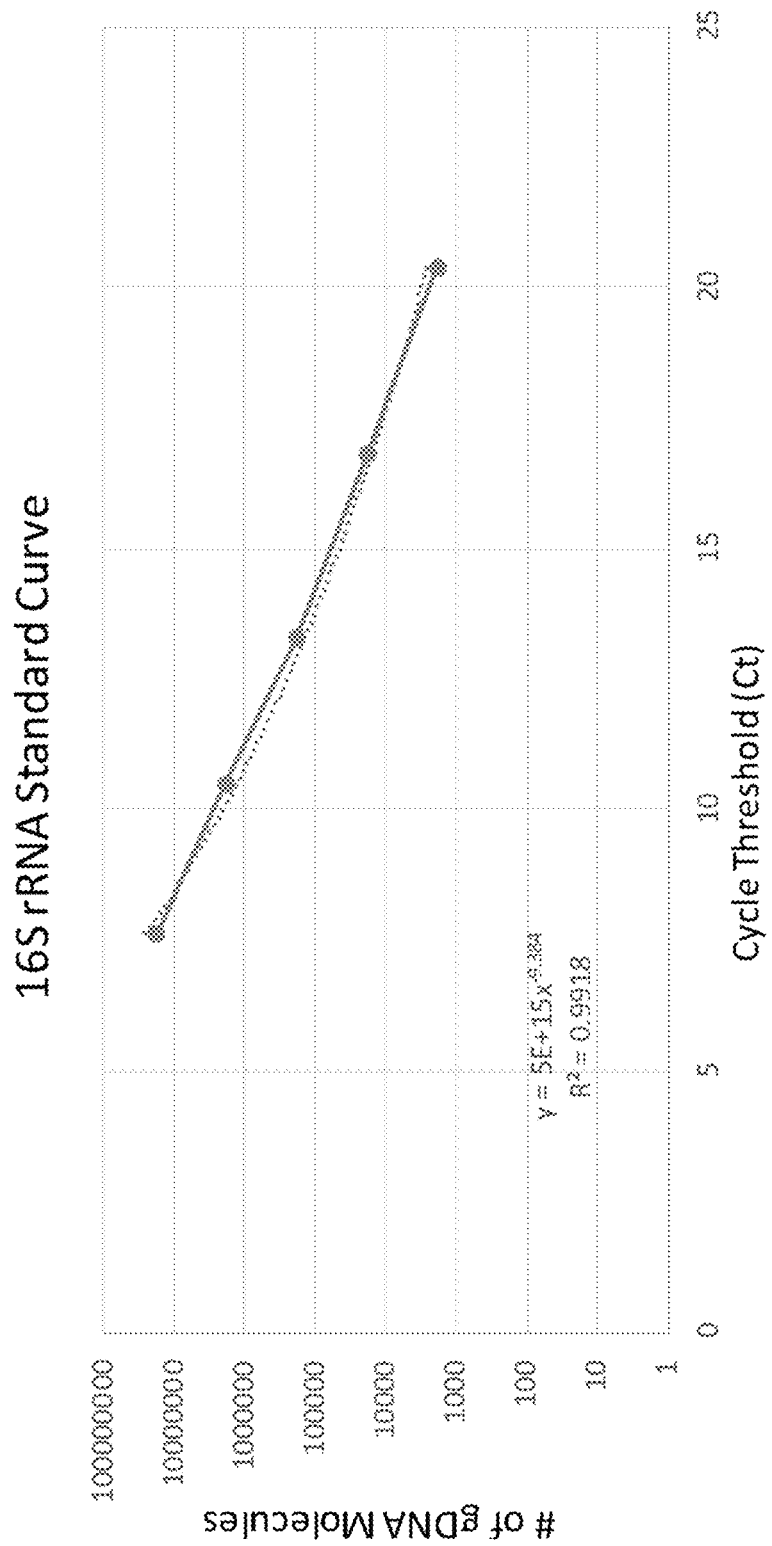
FIG. 5 demonstrates standard curves generated using known amounts of qPCR-amplified genomic DNA. CT values obtained using PMA treated and un-treated samples were used to calculate the number of molecules detected by qPCR amplification.

Live and heat killed CRE showed 9 to 12 Ct difference for 16S and 6 to 7 Ct difference for NDM1. We calculated the number of molecules based on standard curve generated by plotting Ct values against the number of molecules (FIG. 4, FIG. 5). Heat killed CRE showed >99.5% reduction in the number of PCR amenable genomic DNA molecules (Table 3; Live vs Dead (with PMA and enhancer)). The reduction that we saw was specifically due to PMA treatment (Table 4; PMA vs no PMA (with enhancer)). Enhancer significantly increases the effect of PMA.

Figure 6:
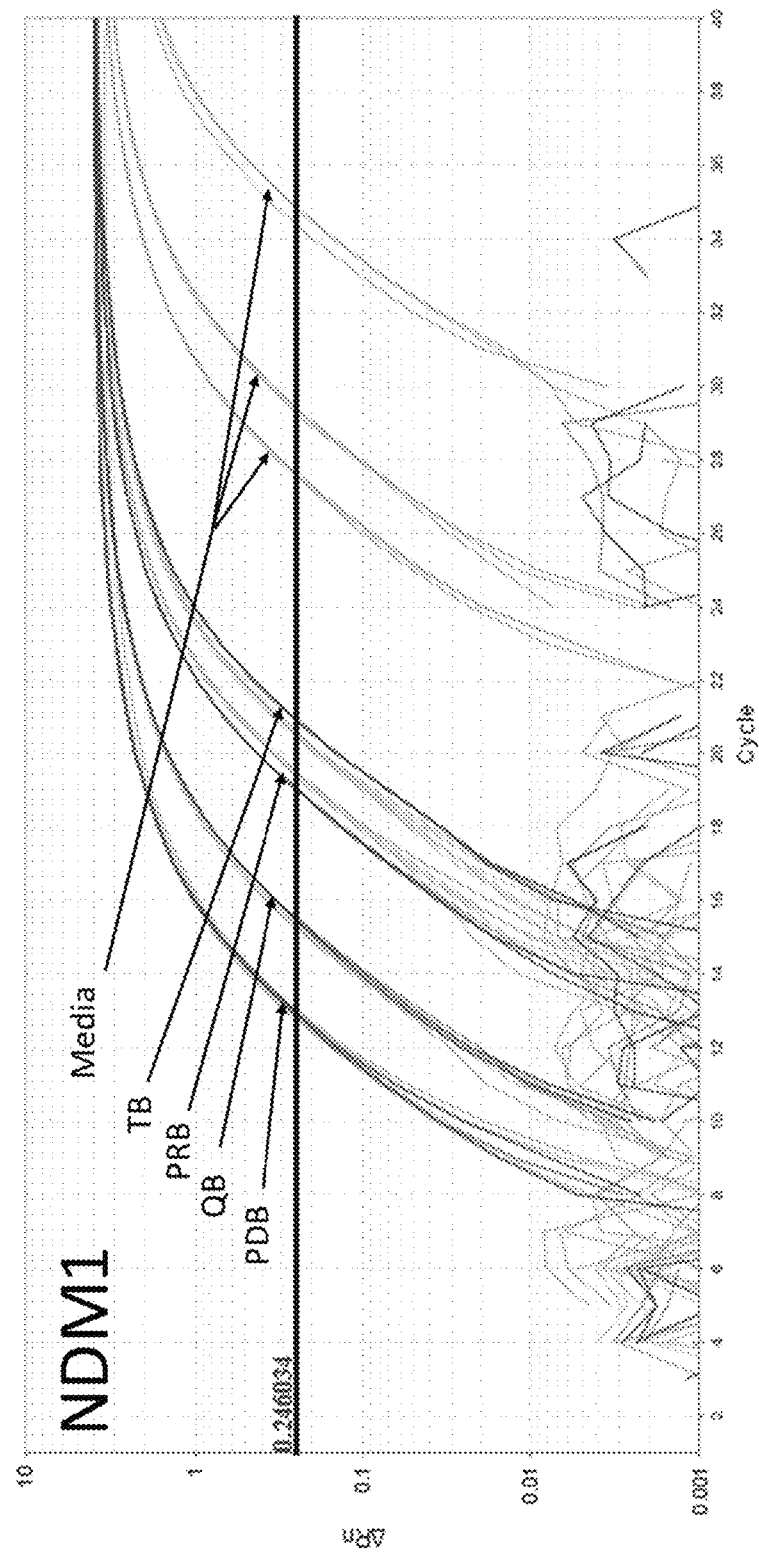
FIGS. 6 and 7 present amplification plots demonstrating efficiency of various DNA extraction methods. Smaller Ct values reflect larger amounts of DNA obtained from extraction.
Figure 7:
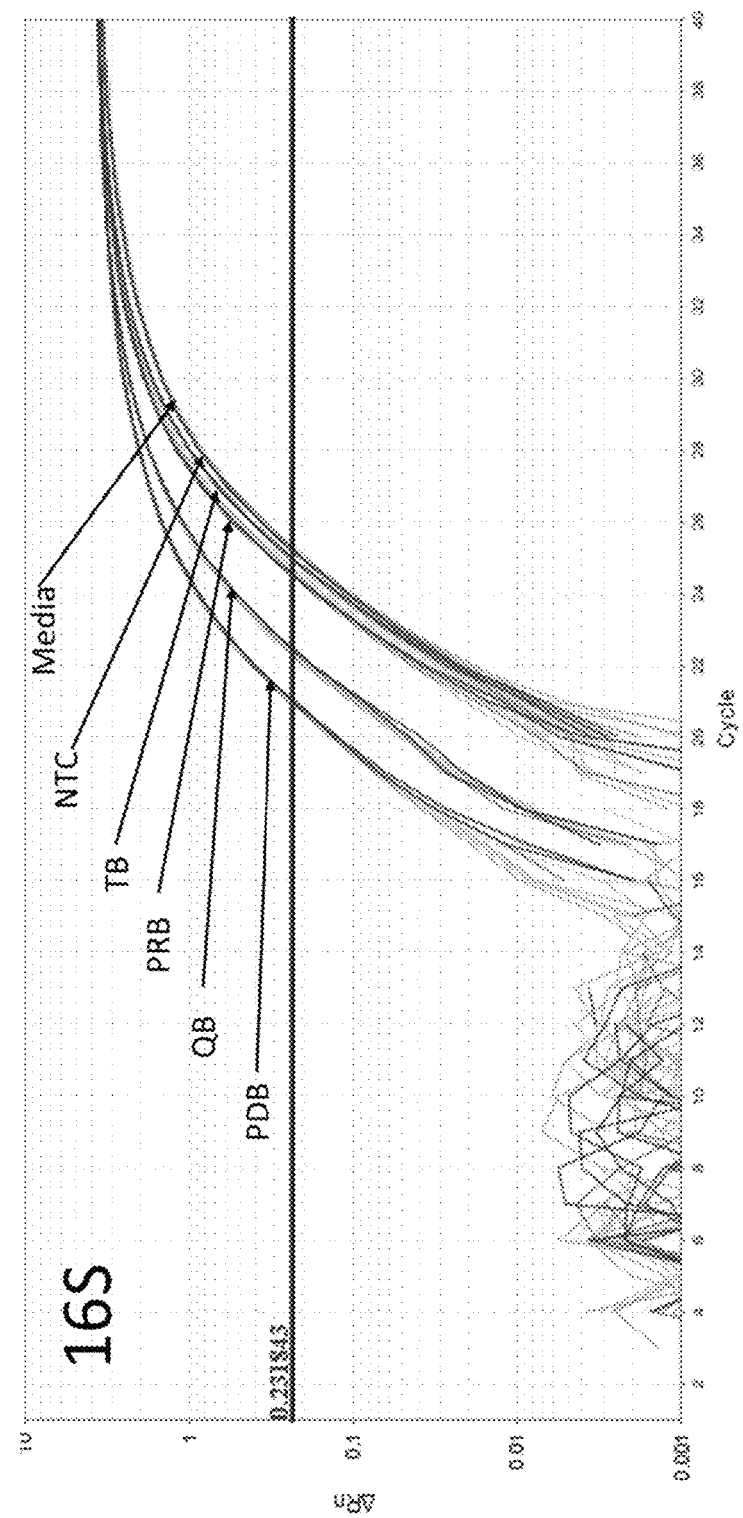

To further improve DNA extraction methods for faster, cost-effective and reproducible generation of qPCR quality DNA, we tested various DNA extraction methods. We tested Qiagen DNA extraction kit, PAXGene DNA extraction kit, PAXGene RNA extraction kit and Trizol reagents. Qiagen DNA extraction method outperformed all other methods in optimum DNA yield (Table 5 and FIGS. 6-7).

We also tested a boiling DNA extraction method and compared it to other commercially available DNA extraction methods. Our boiling DNA extraction method yielded more DNA compared to all commercial DNA extraction methods that we tested (Table 6).

Next we explored DNA extraction efficiency using different numbers of cells and reproducibility using triplicates. DNA extraction method is reproducible and works across different concentrations of cells (Table 7).

Figure 9:
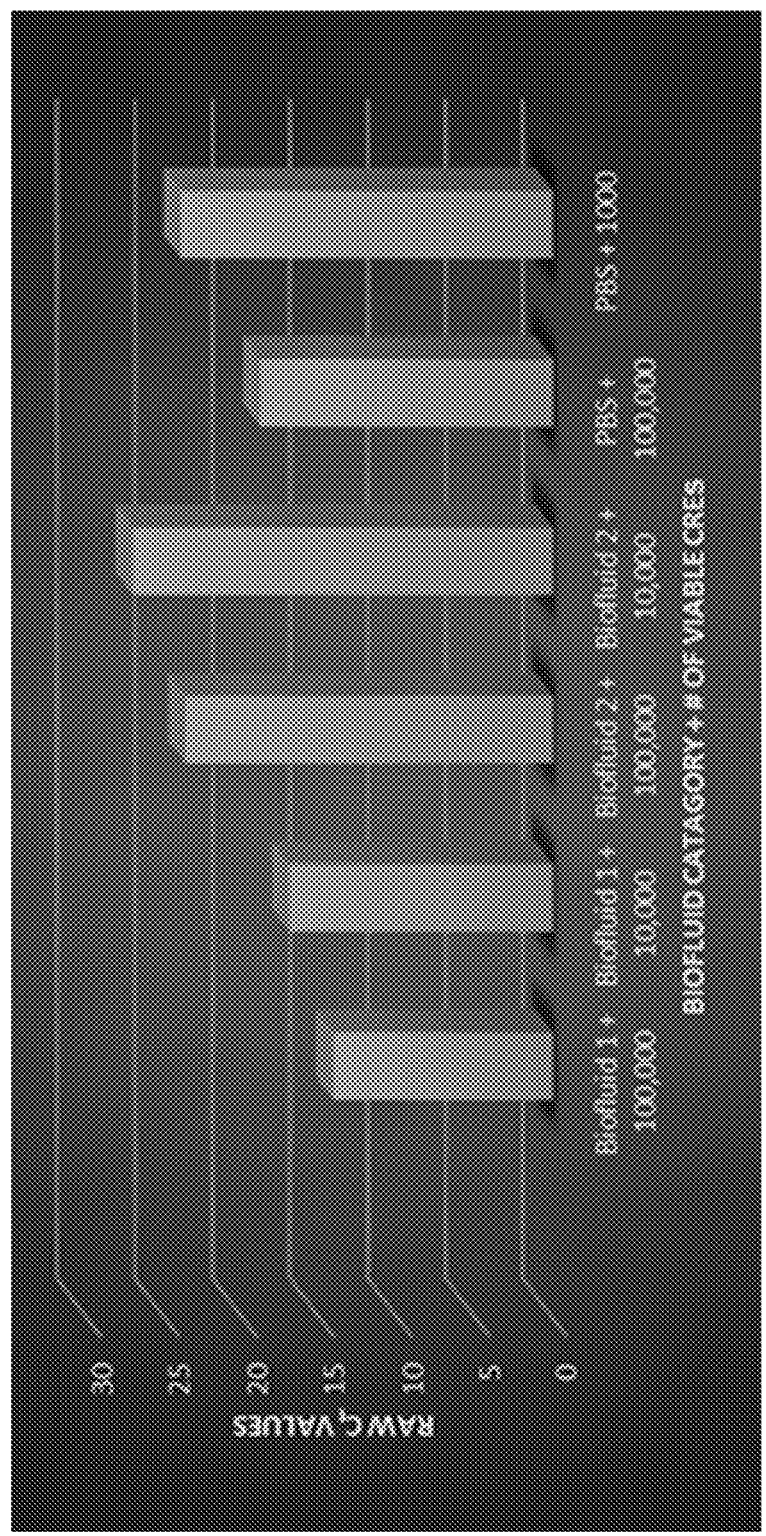
FIG. 9 demonstrates quantitative detection of the number of viable CREs in biological fluids spiked with CREs at different numbers.

By spiking biological fluids with CREs at different numbers, we were able to quantitatively detect the number of viable CREs using our assay. See FIG. 9. This demonstrates our ability to detect viable CREs in biological fluids without any PCR inhibition.

These data demonstrate our development of an improved, reproducible DNA extraction method that yields high quality DNA using an IVD-approved DNA extraction kit to detect and discriminate live and dead CRE. Here we show that when the same number of live and dead bacteria are quantified using our qPCR-based methods, 1.5% of the dead bacteria are detected as compared to the number of live bacteria, where we detect 100%. This suggests that if we have 100 live bacteria, we will detect all of them, but if we have 100 dead bacteria we will detect them (collectively) as 1.5 live bacteria. We are working to improve the detection of dead bacteria to "0" when there is no live bacteria in a population of dead bacteria.

In summary, duodenoscope-related CRE infections are a major public health concern in the United States. It is unlikely that there will be rapid advancements in endoscope design or reprocessing techniques to eliminate the risk of persistent contamination and possible transmission. Development of the reliable, real-time monitoring methods of this disclosure to detect live pathogens on endoscopes will have direct and immediate clinical applicability. The methods described herein have the potential to decrease resource utilization and improve efficiency by identifying CRE-contaminated duodenoscopes and selectively targeting them for sterilization.

TABLE 2

TaqMan Assay Performance and Selection

| Target | Assay ID | PCR Amplification efficiency (%) | Lower Detection limit (# of molecules of genomic DNA) | NTC Amplification (Ct Value >37) |
|---|---|---|---|---|
| NDM1 | AICSXLF | 93 | >10 | Passed |
|  | AIFATXV** | 96 | >10 | Passed |
|  | AIHSQAB | 95 | >10 | Passed |
|  | AIKAMMR | 95 | >10 | Passed |
| KPC1 | AIBJZE7 | 89 | >10 | Passed |
|  | AID1VRN** | 91 | >10 | Passed |
|  | AIGJR33 | 88 | >10 | Passed |
|  | AII10GJ | 87 | >10 | Passed |
| 16S* | AILJKSZ** | 100 and 104 | <1 | Passed |

*Assay tested using two different strains of CRE (NDM1+ KPC− and NDM1− KPC+).
**Selected assays

TABLE 3 qPCR differentiation of live vs dead CRE

| Live or Dead | Treatment | 16S Ct Mean | 16S Difference | NDM1 Ct Mean | NDM1 Difference |
|---|---|---|---|---|---|
| Live vs Dead (with PMA and enhancer) | | | | | |
| Live | Bacteria + Enhancer + PMA | 10.41 | 12.40 | 13.59 | 6.68 |
| Dead | Heat Bacteria + Enhancer + PMA | 22.81 |  | 20.27 |  |
| PMA vs No PMA (with enhancer) | | | | | |
| Dead | Heat Bacteria + Enhancer + PMA | 22.81 | 12.42 | 20.27 | 7.33 |
| Dead | Heat Bacteria + Enhancer | 10.39 |  | 12.94 |  |
| Enhancer vs No Enhancer (with PMA) | | | | | |
| Dead | Heat Bacteria + Enhancer + PMA | 22.81 | 9.66 | 20.27 | 6.04 |
| Dead | Heat Bacteria + PMA | 13.15 |  | 14.23 |  |

TABLE 4

The number of genomic DNA molecules that are not suitable for qPCR by PMA and enhancer treatment

| Live or Dead | Treatment | 16S Assay # of genomic DNA Molecules | 16S Assay % reduction by treatment | NDM1 Assay # of genomic DNA Molecules | NDM1 Assay % reduction by treatment |
|---|---|---|---|---|---|
| Live vs Dead (with PMA and enhancer) | | | | | |
| Live | Bacteria + Enhancer + PMA | 1419960 | 99.94% | 1344610 | 99.53% |
| Dead | Heat killed bacteria + Enhancer + PMA | 900 |  | 6339 |  |

TABLE 4-continued

The number of genomic DNA molecules that are not suitable for qPCR by PMA and enhancer treatment

| Live or Dead | Treatment | 16S Assay # of genomic DNA Molecules | 16S Assay % reduction by treatment | NDM1 Assay # of genomic DNA Molecules | NDM1 Assay % reduction by treatment |
|---|---|---|---|---|---|
| PMA vs No PMA (with enhancer) | | | | | |
| Dead | Heat killed bacteria + Enhancer + PMA | 900 | 99.94% | 6339 | 99.75% |
| Dead | Heat killed bacteria + Enhancer | 1443953 | | 2586418 | |
| Enhancer vs No Enhancer (with PMA) | | | | | |
| Dead | Heat killed bacteria + Enhancer + PMA | 900 | 99.43% | 6339 | 99.12% |
| Dead | Heat killed bacteria + PMA | 158309 | | 721967 | |

TABLE 5

DNA extraction using different commercially available DNA extraction methods

| Methods Used | 16S Average Ct Mean | 16S Ct SD | NDM1 Average Ct Mean | NDM1 Ct SD |
|---|---|---|---|---|
| Qiagen DNA Extraction Method | 22.35 | 0.08 | 15.32 | 0.11 |
| PAXGene DNA Extraction Kit | 20.91 | 0.03 | 12.90 | 0.06 |
| PAXGene RNA Extraction Kit | 24.57 | 0.07 | 19.23 | 0.20 |
| Trizol Reagent | 24.93 | 0.02 | 20.60 | 0.20 |
| No template Control | 25.21 | 0.00 | 30.52 | 3.02 |

TABLE 6

CPD designed boiling DNA extraction method

| DNA extraction Method | 16S Average Ct Mean | 16S Ct SD | NDM1 Average Ct Mean | NDM1 Ct SD |
|---|---|---|---|---|
| Qiagen | 21.7 | 4.1 | 26.0 | 5.1 |
| PAXGene DNA | 24.5 | 0.7 | 31.9 | 5.1 |
| Puregene | 23.2 | 2.3 | 28.7 | 4.9 |
| Boiling Prep | 21.2 | 3.6 | 25.3 | 6.3 |
| NTC | 24.4 | 1.3 | ND | ND |

ND = Not detectable

TABLE 7

CPD designed boiling DNA extraction method works across different concentrations of cells

| Triplicate cell numbers | 16S Mean Ct | 16S SD | 16S Average Ct | 16S SD | NDM1 Mean Ct | NDM1 SD | NDM1 Average Ct | NDM1 SD |
|---|---|---|---|---|---|---|---|---|
| 10K | 20.26 | 0.015 | 19.88 | 0.32 | 22.15 | 0.026 | 22.05 | 0.09 |
| 10K | 19.9 | 0.116 | | | 21.94 | 0.029 | | |
| 10K | 19.47 | 0.005 | | | 22.07 | 0.005 | | |
| 1K | 23.58 | 0.6 | 23.23 | 0.37 | 25.68 | 0.248 | 25.21 | 0.47 |
| 1K | 22.73 | 0.039 | | | 24.57 | 0.025 | | |
| 1K | 23.39 | 0.352 | | | 25.39 | 0.101 | | |
| 100 | 23.43 | 0.061 | 23.7 | 0.27 | 27.56 | 0.081 | 27.18 | 0.39 |
| 100 | 24.07 | 0.385 | | | 27.34 | 0.008 | | |
| 100 | 23.61 | 0.028 | | | 26.64 | 0.005 | | |
| PBS | ND | ND | ND | ND | ND | ND | ND | ND |

ND = Not detectable amplification

We claim:

1. A method for real-time monitoring for live, carbapenem-resistant Enterobacteriaceae (CRE) on a medical device, the method comprising:
   (a) contacting the medical device to an elution buffer;
   (b) collecting the device-contacted elution buffer to create a sample;
   (c) incubating the sample in the presence of a DNA intercalating dye and exposing the contacted sample to light to obtain a light-treated, dye-treated sample;
   (d) centrifuging the light-treated, dye-treated sample to form a pellet of any live or dead bacteria eluted from the medical device;
   (e) resuspending the pellet to form a light-treated, dye-treated suspension;
   (f) extracting genomic DNA from any live or dead bacteria in the light-treated, dye-treated suspension;
   (g) pre-amplifying the extracted genomic DNA, wherein pre-amplifying comprises performing 8 to 12 cycles of target-specific limited amplification using at least two CRE-specific oligonucleotide primers selected from the group consisting of SEQ ID NO:1, SEQ ID NO:2, SEQ ID NO:3, and SEQ ID NO:4 to produce a pre-amplified product; and
   (h) performing quantitative real-time PCR to amplify the pre-amplified product, wherein performing comprises providing the at least two CRE-specific oligonucleotide primers and a probe detectably labeled with a fluorescent dye and a quencher and configured for the real-time PCR reaction using the at least two CRE-specific oligonucleotide primers, wherein the presence of live CRE on the medical device is detected by comparing amplified nucleic acids to a standard curve obtained by quantitative real-time PCR of known quantities of DNA of the live CRE, wherein the method does not comprise culturing the carbapenem-resistant Enterobacteriaceae (CRE).

2. The method of claim 1, wherein the medical device is a duodenoscope.

3. The method of claim 1, wherein the DNA intercalating dye is propidium monoazide (PMA) or ethidium monoazide (EMA).

4. The method of claim 1, wherein step (c) comprises incubating the elution buffer comprising the DNA intercalating dye with an enhancer.

5. The method of claim 1, wherein extracting DNA comprises resuspending the pellet of step (e) with water, and boiling the resuspended pellet at 100° C. for about 15 to about 25 minutes.

6. The method of claim 1, wherein extracting DNA comprises contacting the resuspended pellet of step (e) with a cell lysis solution.

7. The method of claim 2, wherein if the duodenoscope is negative for live CRE, the duodenoscope is not selected for chemical sterilization, and wherein, if the duodenoscope is positive for live CRE, the duodenoscope is selected for chemical sterilization.

8. A method for real-time monitoring for live carbapenem-resistant Enterobacteriaceae (CRE) on a medical device the method comprising:
(a) swabbing the medical device to obtain a sample;
(b) contacting the swab comprising the sample to an elution buffer comprising a DNA intercalating dye;
(c) exposing the elution buffer to light to obtain a light-treated, dye-treated sample;
(d) centrifuging the light-treated, dye-treated sample to form a pellet of any live or dead bacteria eluted from the swab;
(e) resuspending the pellet to form a light-treated, dye-treated sample suspension;
(f) extracting DNA from any live or dead bacteria in the light-treated, dye-treated sample suspension wherein the live or dead bacteria have not been cultured;
(g) pre-amplifying the extracted genomic DNA, wherein pre-amplifying comprises performing 8 to 12 cycles of target-specific limited amplification using at least two CRE-specific oligonucleotide primers selected from the group consisting of SEQ ID NO:1, SEQ ID NO:2, SEQ ID NO:3, and SEQ ID NO:4 to produce a pre-amplified product; and
(h) performing quantitative real-time PCR to amplify the pre-amplified product, wherein performing comprises providing the at least two CRE-specific oligonucleotide primers and a probe detectably labeled with a fluorescent dye and a quencher and configured for the real-time PCR reaction using the at least two CRE-specific oligonucleotide primers, wherein the presence of live CRE in the sample is detected by comparing amplified nucleic acids to a standard curve obtained by quantitative real-time PCR of known quantities of DNA of the live CRE, wherein the method does not comprise culturing the carbapenem-resistant Enterobacteriaceae (CRE).

9. The method of claim 8, wherein the medical device is a duodenoscope.

10. The method of claim 8, wherein the DNA intercalating dye is propidium monoazide (PMA) or ethidium monoazide (EMA).

11. The method of claim 8, wherein step (b) comprises incubating the contacted elution buffer comprising the DNA intercalating dye with an enhancer.

12. The method of claim 8, wherein extracting DNA comprises resuspending the pellet of step (e) with water, and boiling the resuspended pellet at 100° C. for about 15 to about 25 minutes.

13. The method of claim 8, wherein extracting DNA comprises contacting the resuspended pellet of step (e) with a cell lysis solution.

14. The method of claim 9, wherein if the sample is negative for live CRE, the duodenoscope is not selected for chemical sterilization, and wherein, if the sample is positive for live CRE, the duodenoscope is selected for chemical sterilization.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: NDM1 forward primer

<400> SEQUENCE: 1
gacaagatgg gcggtatgga          20

```
-continued

<210> SEQ ID NO 2
<211> LENGTH: 20
<212> TYPE: DNA
<213> ORGANISM: Artificial Sequence
<220> FEATURE:
<223> OTHER INFORMATION: NDM1 reverse primer

<400> SEQUENCE: 2
ctggttcgac aacgcattgg                                                   20

<210> SEQ ID NO 3
<211> LENGTH: 18
<212> TYPE: DNA
<213> ORGANISM: Artificial Sequence
<220> FEATURE:
<223> OTHER INFORMATION: KPC1 forward primer

<400> SEQUENCE: 3
cgccgccaat ttgttgct                                                     18

<210> SEQ ID NO 4
<211> LENGTH: 19
<212> TYPE: DNA
<213> ORGANISM: Artificial Sequence
<220> FEATURE:
<223> OTHER INFORMATION: KPC1 reverse primer

<400> SEQUENCE: 4
gccgatagag cgcatgaag                                                    19

<210> SEQ ID NO 5
<211> LENGTH: 22
<212> TYPE: DNA
<213> ORGANISM: Artificial Sequence
<220> FEATURE:
<223> OTHER INFORMATION: 16S forward primer

<400> SEQUENCE: 5
tggagcatgt ggtttaattc ga                                                22

<210> SEQ ID NO 6
<211> LENGTH: 19
<212> TYPE: DNA
<213> ORGANISM: Artificial Sequence
<220> FEATURE:
<223> OTHER INFORMATION: 16S reverse primer

<400> SEQUENCE: 6
tgcgggactt aacccaaca                                                    19
```